(12) United States Patent
Kuperman et al.

(10) Patent No.: US 7,754,645 B2
(45) Date of Patent: *Jul. 13, 2010

(54) PROCESS FOR PREPARING HYDROPROCESSING BULK CATALYSTS

(75) Inventors: Alexander E. Kuperman, Orinda, CA (US); Jaime Lopez, Benicia, CA (US); Oleg Mironov, Hercules, CA (US); Axel Brait, San Rafael, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 300 days.

This patent is subject to a terminal disclaimer.

(21) Appl. No.: 11/933,085

(22) Filed: Oct. 31, 2007

(65) Prior Publication Data

US 2009/0107891 A1    Apr. 30, 2009

Related U.S. Application Data

(63) Continuation of application No. 11/627,593, filed on Jan. 26, 2007, now Pat. No. 7,396,799, which is a continuation-in-part of application No. 10/938,003, filed on Sep. 10, 2004, now abandoned.

(51) Int. Cl.
*B01J 21/00* (2006.01)
*B01J 31/00* (2006.01)
*B01J 27/24* (2006.01)
*B01J 27/04* (2006.01)

(52) U.S. Cl. ............. 502/200; 502/216; 502/219; 502/220; 502/221; 502/222; 502/223; 502/517; 502/168; 502/3; 502/159; 502/167

(58) Field of Classification Search ............ 502/219, 502/220, 221, 222, 223, 517, 167, 168, 3
See application file for complete search history.

(56) References Cited

U.S. PATENT DOCUMENTS

| | | | |
|---|---|---|---|
| 3,455,677 A | 7/1969 | Litz | |
| 3,673,303 A | 6/1972 | Amano | |
| 3,903,241 A | 9/1975 | Stevens et al. | |
| 4,131,455 A | 12/1978 | Edwards et al. | |
| 4,145,397 A | 3/1979 | Toida et al. | |
| 4,216,118 A | 8/1980 | Yoshida et al. | |
| 4,220,634 A | 9/1980 | Deschamps et al. | |
| 4,409,190 A | 10/1983 | Van Leirsburg | |
| 4,432,953 A | 2/1984 | Hubred et al. | |
| 4,500,495 A | 2/1985 | Hubred et al. | |
| 4,541,868 A | 9/1985 | Lowenhaupt et al. | |
| 4,554,138 A | 11/1985 | Marcantonio | |
| 4,661,265 A | 4/1987 | Olson et al. | |
| 4,762,812 A | 8/1988 | Lopez et al. | |
| 4,801,570 A * | 1/1989 | Young et al. ............. | 502/220 |
| 4,832,925 A | 5/1989 | Weir et al. | |
| 4,861,565 A | 8/1989 | Sefton et al. | |
| 4,900,522 A | 2/1990 | Chou et al. | |
| 5,099,047 A | 3/1992 | Sato et al. | |
| 5,415,849 A | 5/1995 | Toyabe et al. | |
| 5,457,258 A | 10/1995 | Hommeltoft et al. | |
| 5,484,755 A * | 1/1996 | Lopez ............. | 502/219 |
| 5,505,857 A | 4/1996 | Misra et al. | |
| 6,589,492 B2 | 7/2003 | Matsumoto et al. | |
| 6,635,599 B1 * | 10/2003 | Eijsbouts et al. ......... | 502/305 |
| 6,673,732 B2 | 1/2004 | Muhler et al. | |
| 6,733,564 B1 | 5/2004 | Sahu et al. | |
| 7,033,480 B2 | 4/2006 | King et al. | |
| 7,067,090 B2 | 6/2006 | Han et al. | |
| 7,182,926 B2 | 2/2007 | Akahoshi | |
| 7,255,795 B2 | 8/2007 | Sentimenti et al. | |
| 7,396,799 B2 * | 7/2008 | Chen et al. ............. | 502/216 |
| 7,410,928 B2 * | 8/2008 | Chen et al. ............. | 502/216 |
| 7,544,285 B2 * | 6/2009 | Domokos et al. ....... | 208/213 |
| 2003/0130118 A1 | 7/2003 | Koyama et al. | |

(Continued)

FOREIGN PATENT DOCUMENTS

JP    1986-21731    1/1986

(Continued)

OTHER PUBLICATIONS

Hydrodesulfurization Catalysis by Transition Metal Sulfides by Pecoraro et al., Journal of Catalysis 67, 430-445 (1981).

(Continued)

*Primary Examiner*—Elizabeth D Wood

(57) ABSTRACT

A process to prepare hydroprocessing bulk catalysts is provided. The hydroprocessing catalyst has the formula $(M^r)_a (X^u)_b (S^v)_d (C^w)_e (H^x)_f (O^y)_g (N^z)_h$, wherein M is at least one group VIB metal; X is at least at least a metal compound selected from a non-noble Group VIII metal, a Group VIIIB metal, a Group VIB metal, a Group IVB metal, and a Group IIB metal ("Promoter Metal"); t, u, v, w, x, y, z representing the total charge for each of the components (M, X, S, C, H, O and N, respectively); $ta+ub+vd+we+xf+yg+zh=0$; and $0<=b/a<=5$, $(a+0.5b)<=d<=(5a+2b)$, $0<=e<=11(a+b)$, $0<=f<=7(a+b)$, $0<=g<=5(a+b)$, $0<=h<=0.5(a+b)$. In one embodiment, the process comprises the steps of: combining and reacting at least one Group VIB metal compound with at least one group VIII non-noble metal compound to obtain an intermediate mixture; sulfiding the intermediate mixture with a sulfiding agent forming a catalyst precursor; and mixing the catalyst precursor with a hydrocarbon compound to form the hydroprocessing catalyst composition.

21 Claims, 6 Drawing Sheets

U.S. PATENT DOCUMENTS

| | | |
|---|---|---|
| 2004/0219082 A1 | 11/2004 | Matjie et al. |
| 2004/0237720 A1 | 12/2004 | Moyes et al. |
| 2004/0241066 A1 | 12/2004 | Jasra et al. |
| 2005/0118081 A1 | 6/2005 | Harris et al. |
| 2005/0249652 A1 | 11/2005 | Scharifker et al. |
| 2006/0058175 A1 | 3/2006 | Chen et al. |
| 2006/0060503 A1* | 3/2006 | Soled et al. .............. 208/111.3 |
| 2006/0135631 A1 | 6/2006 | Kopponen et al. |
| 2006/0151399 A1 | 7/2006 | Brandts et al. |
| 2006/0258531 A1 | 11/2006 | Koyama et al. |
| 2007/0025899 A1 | 2/2007 | Marcantonio |
| 2007/0098609 A1 | 5/2007 | McConnell |

FOREIGN PATENT DOCUMENTS

| | | |
|---|---|---|
| JP | 06-228666 | 8/1994 |

OTHER PUBLICATIONS

A review of zinc dialkyldithiophosphates (ZDDPS): characterization and role in the lubricating oil by Barnes et al., Tribology International 34 (2001) 389-395.

Petroleum residue upgrading with dispersed catalysts Part I. Catalysts activity and selectivity. Applied Catalysis A: General 204 (2000) 203-213.

Iron sulfide Catalysts for Coal Liquefaction Prepared Using a Micellar Technique by Chadha et al., Ind. Eng. Chem. Res. 1996. 35. 2916-2919.

Nickel, Cadium and Lead Sulfides as Catalysts in the Vapor Phase Reduction of Nitrobenzene by Brown et al., Laboratory of Physical Chemistry. Indiana University. Jul. 29, 1938.

Solution Synthesis of the unsupported Ni-W sulfide hytrotreating catalysts by Le et al., Catalysis Today 130 (2008) 24-31.

Thermal decomposition of sulfur comppunds. I. 2-Methyl-2-propanethiol by Thompson et al., Bureau of Mines. Petroleum and Oil-Shale Experiment Station, Nov. 19, 1951.

Hydroprocessing of heavy petroleum feeds: tutorial by Ancheyta et al. Catalysis today 109 (2005) 3-15.

A review of recent advances on process technologies for upgrading of heavy oils and residue by Rana et al., Fuel 86 (2007) 1216-1231.

* cited by examiner

US 7,754,645 B2

PROCESS FOR PREPARING HYDROPROCESSING BULK CATALYSTS

CROSS-REFERENCE TO RELATED APPLICATIONS

This application is a continuation-in-part of application Ser. No. 12/168,687 filed Jul. 7, 2008, pending, which is a continuation of application Ser. No. 11/627,593 filed Jan. 26, 2007, now U.S. Pat. No. 7,396,799, which is a continuation-in-part of application Ser. No. 10/938,003 filed Sep. 10, 2004, abandoned.

TECHNICAL FIELD

The invention relates generally to a process for preparing bulk catalysts for use in the conversion of heavy oils and residua.

BACKGROUND

The petroleum industry is increasingly turning to heavy crudes, resids, coals and tar sands as sources for feedstocks. Feedstocks derived from these heavy materials contain more sulfur and nitrogen than feedstocks derived from more conventional crude oils, requiring a considerable amount of upgrading in order to obtain usable products therefrom. The upgrading or refining generally being accomplished by hydrotreating processes, i.e., treating with hydrogen of various hydrocarbon fractions, or whole heavy feeds, or feedstocks, in the presence of hydrotreating catalysts to effect conversion of at least a portion of the feeds, or feedstocks to lower molecular weight hydrocarbons, or to effect the removal of unwanted components, or compounds, or their conversion to innocuous or less undesirable compounds.

Catalyst precursors commonly used for these hydrotreating reactions include materials such as cobalt molybdate on alumina, nickel oil alumina, cobalt molybdate promoted with nickel, nickel tungstate, etc. U.S. Pat. Nos. 4,824,821 and 5,484,755 and US Patent Publication No. 2006/0054535 disclose hydroprocessing catalysts in the form of high activity slurry. The slurry catalyst is produced from group VIB metal compounds by sulfiding an aqueous mixture of the metal compound with hydrogen sulfide ($H_2S$) gas at a pressure of up to 5,000 psi (340 atm).

US Patent Publication No. 20070161505 discloses an ultra-dispersed catalyst composition having a median particle diameter between 30-6000 nm, prepared by mixing separate micro-emulsions of Group VIB or VIIIB non-noble metals. Each micro-emulsion is prepared by mixing solutions containing either Group VIB or VIIIB metal with a hydrocarbon feedstock. As the metals were sulfided separately, when the micro-emulsions are mixed together, a first metal component (e.g., NiS) simply deposits on the outer layer of the second metal component (e.g., $MoS_2$), thus forming a "core shell" type catalyst structure. Core-shell type catalysts formed with pre-sulfided metal components have lower catalytic activity than catalysts formed in a process wherein the metals are allowed to react/in contact with each other prior to sulfidation to form a more homogeneous structure.

There is still a need for improved process to prepare catalysts having the appropriate morphology, structure, and optimum catalytic activity for high yield conversions.

SUMMARY OF THE INVENTION

In one aspect, there is provided a process for preparing a hydroprocessing catalyst composition, which process comprising the steps of combining and reacting at least one Group VIB metal compound with at least a metal compound selected from a non-noble Group VIII metal, a Group VIIIB metal, a Group VIB metal, a Group IVB metal, and a Group IIB metal ("Promoter Metal"), to obtain an intermediate mixture; sulfiding the intermediate mixture with a sulfiding agent forming a catalyst precursor; and iii) mixing the catalyst precursor with a hydrocarbon compound to form a catalyst composition having formula $(M^t)_a(X^u)_b(S^v)_d(C^w)_e(H^x)_f(O^y)_g(N^z)_h$, wherein the molar ratio of the sulfiding agent to the at least one Group VIB metal compound and the at least a Promoter Metal compound is sufficient for subscript d to have a value of: $(a+0.5b) \leq d \leq (5a+2b)$, and wherein the catalyst precursor is mixed with a sufficient amount of hydrocarbon for subscript e to have a value of $0 \leq e \leq 11(a+b)$. In the formula, subscripts a and b each are suitably greater than 0 such that $0 \leq b/a \leq 5$, $0 \leq f \leq 7(a+b)$, $0 \leq g \leq 5(a+b)$, $0 \leq h \leq 0.5(a+b)$; t, u, v, w, x, y, z representing the total charge for each of the components (M, X, S, C, H, O and N, respectively); and $ta+ub+vd+we+xf+yg+zh=0$.

In another aspect, there is provided a process for preparing a hydroprocessing catalyst having the formula $(M^t)_a(X^u)_b(S^v)_d(C^w)_e(H^x)_f(O^y)_g(N^z)_h$, wherein M is selected from molybdenum, tungsten, and mixtures thereof and X is selected from nickel, cobalt, and mixture thereof, and wherein the sulfiding agent is ammonium sulfide.

DETAILED DESCRIPTION

Figure 1:
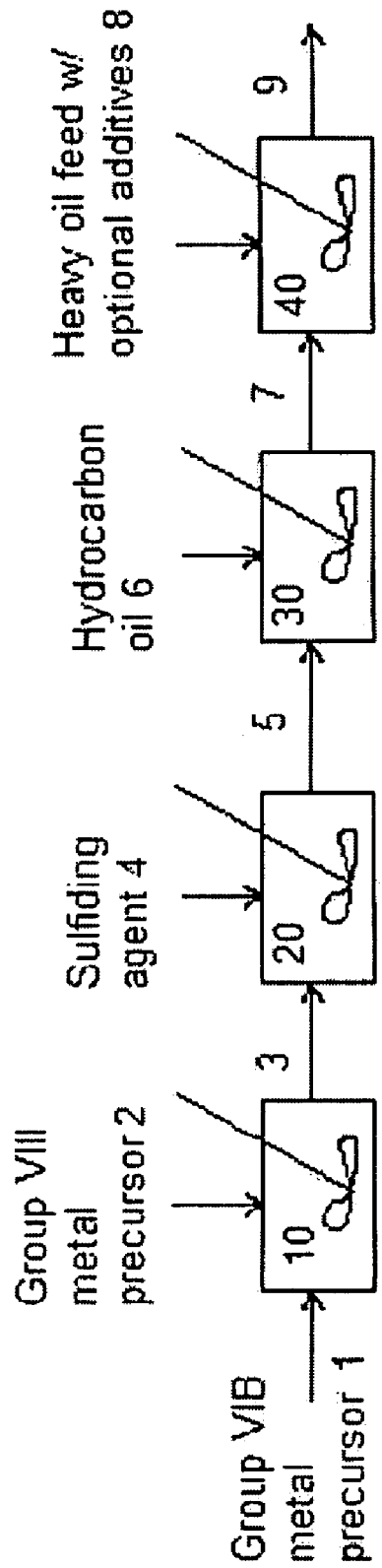
FIG. 1 illustrates the steps involved in an embodiment for preparing the catalyst composition.

The following terms will be used throughout the specification and will have the following meanings unless otherwise indicated.

As used herein, "hydroprocessing" is meant any process that is carried out in the presence of hydrogen, including, but not limited to, methanation, water gas shift reactions, hydrogenation, hydrotreating, hydrodesulfurization, hydrodenitrogenation, hydrodemetallation, hydrodearomatization, hydroisomerization, hydrodewaxing and hydrocracking including selective hydrocracking. Depending on the type of hydroprocessing and the reaction conditions, the products of hydroprocessing may show improved viscosities, viscosity indices, saturates content, low temperature properties, volatilities and depolarization, etc.

As used here, the term "bulk catalyst" may be used interchangeably with "unsupported catalyst," meaning that the catalyst composition is NOT of the conventional catalyst form which has a preformed, shaped catalyst support which is then loaded with metals via impregnation or deposition catalyst. In one embodiment, the bulk catalyst is formed through precipitation. In another embodiment, the bulk catalyst has a binder incorporated into the catalyst composition. In yet another embodiment, the bulk catalyst is formed from metal compounds and without any binder. In a fourth embodiment, the bulk catalyst is a dispersing-type catalyst ("slurry catalyst") for use as dispersed catalyst particles in mixture of liquid (e.g., hydrocarbon oil).

As used herein, the term "catalyst precursor" refers to a compound containing one or more catalytically active metals, from which compound the catalyst of the invention having the formula $(M^t)_a(X^u)_b(S^v)_d(C^w)_e(H^x)_f(O^y)_g(N^z)_h$, is eventually formed, and which compound may be catalytically active as a hydroprocessing catalyst.

As used herein, the phrase "one or more of" or "at least one of" when used to preface several elements or classes of elements such as X, Y and Z or $X_1$-$X_n$, $Y_1$-$Y_n$ and $Z_1$-$Z_n$, is intended to refer to a single element selected from X or Y or Z, a combination of elements selected from the same common class (such as $X_1$ and $X_2$), as well as a combination of elements selected from different classes (such as $X_1$, $Y_2$ and $Z_n$).

Catalyst Formula: In one embodiment, the catalyst composition as expressed in elemental form, is of the general formula $(M^t)_a(X^u)_b(S^v)^*_d(C^w)_e(H^x)_f(O^y)_g(N^z)_h$. The formula herein refers to the catalyst solids, constituting the catalyst slurry in oil, prepared by the method described below. In the equation, M represents at least one group VIB metal, such as Mo, W, etc. or a combination thereof; and X functions as a promoter metal, representing at least one of: a non-noble Group VIII metal such as Ni, Co; a Group VIIIB metal such as Fe; a Group VIB metal such as Cr, a Group IVB metal such as Ti; a Group IIB metal such as Zn, and combinations thereof (X is hereinafter referred to as "Promoter Metal"). Also in the equation, t, u, v, w, x, y, z representing the total charge for each of the component (M, X, S, C, H, O and N, respectively); ta+ub+vd+we+xf+yg+zh=0. The subscripts ratio of b to a has a value of 0 to 5 (0<=b/a<=5). S represents sulfur with the value of the subscript d ranging from (a+0.5b) to (5a+2b). C represents carbon with subscript e having a value of 0 to 11(a+b). H is hydrogen with the value of f ranging from 0 to 7(a+b). O represents oxygen with the value of g ranging from 0 to 5(a+b); and N represents nitrogen with h having a value of 0 to 0.5(a+b).

In one embodiment, a and b each are suitably greater than 0 such that the ratio of a:b is in the range of 1:5 to 10:1. For example, in one embodiment with b/a having a value of 0.2, a has a value of 5 and b has a value of 1. Thus, at this b/a ratio of 0.2, $(M^t)_a(X^u)_b(S^v)_d(C^w)_e(H^x)_f(O^y)_g(N^z)_h$ would include compositions ranging from $(M)_5(X)(S)_{5.5}$, including $(M)_5(X)(S)_{5.5}(C)(H)(O)(N)$, to $(M)_5(X)(S)_{27}(C)_{66}(H)_{42}(O)_{30}(N)_3$.

In one embodiment, M is at least one or two metals selected from chromium, molybdenum and tungsten. In a second embodiment, M is selected from molybdenum, tungsten and a combination of the two. In yet another embodiment, M is molybdenum.

In one embodiment where both molybdenum and tungsten are used, the catalyst is of the formula $(Mo_zW_{1-z})_a(X)_b(S)_d(C)_e(H)_f(O)_g(N)_h$, where 0<z<1. In yet another embodiment where M is a mixture of Mo and W, the molybdenum to tungsten ratio is in the range of 9:1-1:9.

In one embodiment, X is at least one or two non-noble metals selected from nickel, cobalt and iron. In a second embodiment, X is selected from nickel, cobalt and a combination of nickel and cobalt. In a third embodiment, X is nickel. In one embodiment where X is a mixture of two metals such as Ni and Co, the catalyst is of the formula $(M)_a(Ni_zCo_{1-z})_b(S)_d(C)_e(H)_f(O)_g(N)_h$, where 0<z<1. In another embodiment where X is a mixture of multiple metals such as Ni, Co, Fe, Zn, Cr, Ti, the catalyst is of the formula $(M)_a(Ni_zCo_{z'}Fe_{z''}Zn_{z^*}Cr_{z^*'}Ti_{z^*''})_b(S)_d(C)_e(H)_f(O)_g(N)_h$, where $0 \leq z, z', z'', z^*, z^{*'}, z^{*''}$ and $(z+z'+z''+z^*+z^{*'}+z^{*''})=1$.

In the sections that follow, the reference to "molybdenum" is by way of exemplification only for component (M) in the formula $(M^t)_a(X^u)_b(S^v)_d(C^w)_e(H^x)_f(O^y)_g(N^z)_h$, and is not intended to exclude other Group VIB metals/compounds and mixtures of Group VIB metal/compounds represented by (M) in the catalyst formula. Similarly, the reference to "nickel" is by way of exemplification only for the component (X) in the formula $(M^t)_a(X^u)_b(S^v)_d(C^w)_e(H^x)_f(O^y)_g(N^z)_h$, and is not meant to exclude other Promoter Metals, i.e., group VIII non-noble metal components, Group VIIIB metals; Group VIB metals; Group IVB metals; Group IIB metals and mixtures thereof that can be used in the catalyst formula.

The sections that follow describe reagents that can be used in the manufacture $(M^t)_a(X^u)_b(S^v)_d(C^w)_e(H^x)_f(O^y)_g(N^z)_h$. The term reagent refers to a raw material that can be used in the manufacture of the catalyst. As used herein, the term "metal" does not mean that the reagent is in the metallic form, but is present as a metal compound. Also as used herein, the term "metal" or "metal precursor" in the singular form is not limited to a single metal or metal precursor, i.e., Group VIB or Promoter Metals, but also includes the plural references for mixtures of metals. As used herein, "in the solute state" means that the metal component is in a protic liquid form. Also as used herein, the term "metal precursor" refers to the metal compound feed to the process.

Group VIB Transition Metal/Precursor Component: In one embodiment, at least part of the Group VIB transition (M) metal precursor is added in the solid state. In a second embodiment, at least part of the group VIB metal precursor is added in the solute state. In one embodiment, the molar ratio of Group VIB metal to Promoter Metal is in the range of 9:1-1:9. In a second embodiment, the molar ratio is in the range of 3:1 to 1:3.

In one embodiment, (M) metal precursor is selected from molybdenum and/or tungsten components, e.g., alkali metal or ammonium metallates of molybdenum, (e.g., ammonium molybdate and also iso-, peroxo-, di-, tri-, tetra-, hepta-, octa-, or tetradecamolybdate), ammonium salts of phosphomolybdic acids, Mo—P heteropolyanion compounds, Wo—Si heteropolyanion compounds, W—P heteropolyanion compounds. W—Si heteropolyanion compounds; Ni—Mo—W heteropolyanion compounds. Co—Mo—W heteropolyanion compounds, alkali metal or ammonium tungstates (also meta-, para-, hexa-, or polytungstate), or mixtures thereof, added in the solute state such as water-soluble molybdenum and tungsten compounds.

In one embodiment, the (M) metal precursor is selected from the group of alkali metal or ammonium metallates of molybdenum in organic solvents such as a normal alkane, hydrocarbons, or petroleum products such as distillate fractions wherein the molybdenum compound is allowed to subsequently decompose under pressure and temperature, prior to or concurrent with the addition of the Promoter Metal precursor.

In yet another embodiment, the group VIB metal precursor is selected from the group of alkali metal heptamolybdates, alkali metal orthomolybdates, alkali metal isomolybdates, phosphomolybdic acid, and mixtures thereof. In a fourth embodiment, it is selected from the group of molybdenum (di- and tri) oxide, molybdenum carbide, molybdenum nitride, aluminum molybdate, molybdic acid (e.g. $H_2MoO_4$), or mixtures thereof.

In one embodiment, the (M) precursor is a water-soluble ammonium heptamolybdate $[(NH_4)_6Mo_7O_{24}\cdot 4H_2O]$. In another embodiment, it is ammonium thiomolybdate. In yet another embodiment, it is a polyalkyl thiomolybdate.

Promoter Metal Precursor Component: In one embodiment, the Promoter Metal (X) precursor is in a solute state, wherein the whole amount of the metal precursor is in a protic liquid form, and wherein the metal is at least partly present as a solid and partly dissolved in the protic liquid in one embodiment.

In one embodiment, the (X) metal precursor is a metal salt or mixtures selected from nitrates, hydrated nitrates, chlorides, hydrated chlorides, sulfates, hydrated sulfates, formates, acetates, hypophosphites, and mixtures thereof, added in a solute state Examples include water-soluble nickel and/or cobalt components, e.g. water-soluble nickel and/or cobalt salts such as nitrates, sulfates, acetates, chlorides, formates or mixtures thereof of nickel and/or cobalt as well as nickel hypophosphite.

In one embodiment, the (X) metal precursor is a water-soluble nickel component, e.g. nickel nitrate, nickel sulfate, nickel acetate, nickel chloride, or mixtures thereof. In another embodiment, the metal precursor is a nickel compound which is at least partly in the solid state, e.g., a water-insoluble nickel compound such as nickel carbonate, nickel hydroxide, nickel phosphate, nickel phosphite, nickel formiate, nickel sulfide, nickel molybdate, nickel tungstate, nickel oxide, nickel alloys such as nickel-molybdenum alloys, Raney nickel, or mixtures thereof. In a third embodiment, the metal precursor containing (X) is a water-soluble nickel sulfate solution. In yet another embodiment, another Promoter Metal compound is added to the water-soluble reagent, e.g., an iron component in the solute state selected from iron acetate, chloride, formate, nitrate, sulfate and mixtures thereof.

In one embodiment, the (X) metal precursor is a nickel sulfate aqueous solution.

Sulfiding Agent Component: In one embodiment, the sulfiding agent is in the form of a solution which under prevailing conditions is decomposable into hydrogen sulfide, present in an amount in excess of the stoichiometric amount required to form the catalyst. In one embodiment, the amount represents a sulfur to molybdenum mole ratio of at least 3 to 1 to produce a catalyst precursor.

In one embodiment, the sulfiding agent is selected from the group of ammonium sulfide, ammonium polysulfide $((NH_4)_2S_x)$, ammonium thiosulfate $((NH_4)_2S_2O_3)$, sodium thiosulfate $(Na_2S_2O_3)$, thiourea $(CSN_2H_4)$, carbon disulfide $(CS_2)$, dimethyl disulfide (DMDS), dimethyl sulfide (DMS), tertiarybutyl polysulfide (PSTB) and tertiarynonyl polysulfide (PSTN), and mixtures thereof. In another embodiment, the sulfiding agent is selected from alkali- and/or alkaline earth metal sulfides, alkali- and/or alkaline earth metal hydrogen sulfides, and mixtures thereof. The use of sulfiding agents containing alkali- and/or alkaline earth metals may require an additional separation process step to remove the alkali- and/or alkaline earth metals from the spent catalyst.

In one embodiment, the sulfiding agent is ammonium sulfide in aqueous solution. An aqueous ammonium sulfide solution can be synthesized from hydrogen sulfide and ammonia—common refinery off-gases. This synthesized ammonium sulfide is readily soluble in water and can easily be stored in aqueous solution in tanks prior to use. Since ammonium sulfide solution is more dense than resid, it can be separated easily in a settler tank after reaction.

Optional Component—Binder Material: In one embodiment, a binder is optionally included in the process for making the catalyst. Generally, the binder material has less catalytic activity than the catalyst composition (without the binder material) or no catalytic activity at all. Consequently, by adding a binder material, the activity of the catalyst composition may be reduced. Therefore, the amount of binder material to be added in the process of the invention generally depends on the desired activity of the final catalyst composition. Binder amounts from 0-95 wt. % of the total composition can be suitable, depending on the envisaged catalytic application. In another embodiment, binder can be optionally added in the range of 0.5-75 wt. % of the total composition.

The binder materials can be added to the metal precursors either simultaneously or one after the other. Alternatively, the metal precursors can be combined together and subsequently a binder material can be added to the combined metal precursors. It is also possible to combine part of the metal precursors either simultaneously or one after the other, to subsequently add the binder material and to finally add the rest of the metal precursors either simultaneously or one after the other. Furthermore, it is also possible to combine the binder with metal precursors in the solute state and to subsequently add a metal precursor at least partly in the solid state.

In one embodiment, the binder material is mixed with a Group VIB metal and/or a Promoter Metal, e.g., a Group VIII non-noble metal, prior to being mixed with the bulk catalyst composition and/or prior to being added during the preparation thereof. Compositing the binder material with any of these metals in one embodiment is carried out by impregnation of the solid binder with these materials.

Optional binder materials include any materials that are conventionally applied as a binder in hydroprocessing catalysts. Examples include silica, silica-alumina, such as conventional silica-alumina, silica-coated alumina and alumina-coated silica, alumina such as (pseudo)boehmite, or gibbsite, titania, zirconia, cationic clays or anionic clays such as saponite, bentonite, kaoline, sepiolite or hydrotalcite, or mixtures thereof. In one embodiment, binder materials are selected from silica, colloidal silica doped with aluminum, silica-alumina, alumina, titanium, zirconia, or mixtures thereof. In one embodiment, the catalyst comprises a refractory oxide material which comprises 50 wt. % or more titania, on oxide basis.

These binders may be applied as such or after peptization. It is also possible to apply precursors of these binders that, during the process of the invention are converted into any of the above-described binders. Suitable precursors are, e g., alkali metal aluminates (to obtain an alumina binder), water glass (to obtain a silica binder), a mixture of alkali metal aluminates and water glass (to obtain a silica alumina binder), a mixture of sources of a di-, tri-, and/or tetravalent metal such as a mixture of water-soluble salts of magnesium, aluminum and/or silicon (to prepare a cationic clay and/or anionic clay), chlorhydrol, aluminum sulfate, or mixtures thereof.

In one embodiment with the incorporation of a binder or binders, the catalyst is of the formula $(M^r)_a(X^n)_b(Z)_c(S^v)_d(C^w)_e(H^x)_f(O^y)_g(N^z)_h$, with Z representing titanium and optionally one or more elements selected from aluminum, silicon, magnesium, zirconium, boron, and zinc.

In one embodiment where alumina is used as a binder, the alumina binder has a surface area ranging from 100 to 400 $m^2/g$, with a pore volume ranging from 0.5 to 1.5 ml/g measured by nitrogen adsorption. In one embodiment where titania is used as a binder, the titania has an average particle size of less than 50 microns. In a second embodiment, the titania binder has an average particle size of less than 5 microns. In a third embodiment, the titania binder has an average particle size of greater than 0.005 microns. In a fourth embodiment, the titania binder has a BET surface area of 10 to 700 m$^2$/g.

Component—Hydrocarbon Transforming Agent: The hydrocarbon transforming agent transforms the catalyst precursor (hydrophilic) to an oil based active catalyst (hydrophobic) of the formula $(M)_a(X)_b(S)_d(C)_e(H)_f(O)_g(N)_h$. The nature of the hydrocarbon is not critical, and can generally include any hydrocarbon compound, acyclic or cyclic, saturated or unsaturated, unsubstituted or inertly substituted, and mixtures thereof, and which hydrocarbon compound is liquid at ordinary temperatures. In one embodiment, the weight ratio of the water base catalyst precursor to the hydrocarbon compound is in the range of 1:10 to 5:1. In a second embodiment, the weight ratio of the water base catalyst precursor to the hydrocarbon compound is in the range of 1:5 to 1:1.

In one example, the hydrocarbon compound is selected from the group of straight chain saturated acyclic hydrocarbons as octane, tridecane, eicosane, nonacosane, or the like; straight chain unsaturated acyclic hydrocarbons as 2-hexene, 1,4-hexadiene, and the like; branched chain saturated acyclic hydrocarbons as 3-methylpentane, neopentane, isohexane, 2,7,8-triethyldecane, and the like; branched chain unsaturated acyclic hydrocarbons such as 3,4-dipropyl-1,3-hexadiene-5-yne, 5,5-dimethyl-1-hexene, and the like; cyclic hydrocarbons, saturated or unsaturated, such as cyclohexane, 1,3-cyclohexadiene, and the like; and including such aromatics as cumene, mesitylene, styrene, toluene, o-xylene, or the like. In yet another embodiment, the hydrocarbon compound is derived from petroleum, including admixtures of petroleum hydrocarbons characterized as virgin naphibas, cracked naphthas, Fischer-Tropsch naphtha, light cat cycle oil, heavy cat cycle oil, and the like, typically those containing from about 5 to about 30 carbon atoms.

In one embodiment, the hydrocarbon compound has a kinetic viscosity ranging from 2 cSt to 15 cSt @ 100° C. In a second embodiment, the hydrocarbon oil has a kinematic viscosity of at least 2 cSt at 100° C. In a third embodiment, from 5 cSt to 8 cSt at 100° C. The hydrocarbon oil causes a transformation of the catalyst precursor from a water based to an oil based. In one embodiment, the ratio of the Group VIB metal (M) to hydrocarbon is less than 1.0. In a second embodiment, the ratio is less than 0.5. In a third, less than 0.1. In one embodiment with the kinematic viscosity of the hydrocarbon transforming agent being below 2 cSt @ 100° C. or above about 15 cSt @ 100° C., the transformation of the catalyst precursor results in catalyst particles agglomerating or otherwise not mixing. In one embodiment, the hydrocarbon compound is a vacuum gas oil (VGO).

Optional Components: If desired, materials including other metals can be added in addition to the components described above. These materials include any material that is added during conventional hydroprocessing catalyst preparation. Suitable examples are phosphorus compounds, boron compounds, additional transition metals, rare earth metals or mixtures thereof. Suitable phosphorus compounds include ammonium phosphate, phosphoric acid, or organic phosphorus compounds. Suitable additional transition metals that can be added to the process steps include are, e.g., rhenium, ruthenium, rhodium, iridium, chromium, vanadium, iron, cobalt, platinum, palladium, and cobalt. In one embodiment, the additional metals are applied in the form of water-insoluble compounds. In another embodiment, the additional metals are added in the form of water soluble compounds. Apart from adding these metals during the process, it is also possible to composite the final catalyst composition therewith the optional materials. It is, e.g., possible to impregnate the final catalyst composition with an impregnation solution comprising any of these additional materials.

In one embodiment to help reduce coking, the additional optional component added is phosphorous in the form of phosphomolybdic acid having an atomic ratio of P/Mo ranging from about 0.08:1 to 0.01:1.

Method for Making Hydroprocessing Catalyst: In one embodiment, the preparation method allows systematic varying of the composition and structure of the catalyst by controlling the relative amounts of the elements, the types of the feed components (reagents), the length and severity of the various reactions.

a. Forming a Precipitate with Group VIB Metal/Promoter Metal: In one embodiment of the process, the first step is a precipitation step, which involves reacting in a mixture the Promoter Metal component in solution and the Group VIB metal component in solution to obtain a precipitate or slurry. In one embodiment, the precipitate or slurry is in aqueous solution. The precipitation is carried out at a temperature and pH, at which the Promoter Metal compound and the Group VIB metal compound precipitate. In another embodiment, at least one metal component is added in the solid state and at least one metal component is added in a solute state.

The precipitation reaction is in the range of 0-300° C. in one embodiment, between 25-200° C. in a second embodiment, and in the range of 70-180° C. in a third embodiment. If the temperature is below the boiling point of the protic liquid, such as 100° C. in the case of water, the process is generally carried out at atmospheric pressure. Above this temperature, the reaction is generally carried out at increased pressure, such as in an autoclave. In one embodiment, the precipitation reaction is at between 0 to 3000 psig. In a second embodiment, between 100 to 1000 psig.

In one embodiment, the mixture is kept at its natural pH during the reaction step. The pH is in the range of 0-12 in one embodiment, between 2-10 in a second embodiment, and 3-8 in a third embodiment. Changing the pH can be done by adding base or acid to the reaction mixture, or adding compounds, which decompose upon temperature increase into hydroxide ions or $H^+$ ions that respectively increase or decrease the pH. Examples include urea, nitrites, ammonium hydroxide, etc. In one embodiment, the pH is controlled such that the pH at the beginning of the reaction differs from the final pH after precipitation.

In one embodiment, the reaction of the Group VIB and the Promoter Metal components is carried out with water-soluble nickel, molybdenum and tungsten components under conditions described above. The solution may further comprise other Promoter Metal components, e.g., cobalt or iron components such as $Co(NO_3)_2$, $Co(CH_3CO_2)_2$, or chromium components. In one embodiment, the reaction of the Group VIB and the Promoter Metal component is in an organic solvent with added water under $H_2$-containing gas pressure, with the organic solvent being a hydrocarbon mixture of alkanes and aromatic compounds.

In one embodiment, the reaction is carried with the appropriate metal precursors resulting in precipitate combinations of nickel/molybdenum/tungsten, cobalt/molybdenum/tungsten or nickel/cobalt/molybdenum/tungsten. These types of precipitates have a higher surface area than precipitates prepared from the Group VIB metal and the Promoter Metal, e.g., a group non-noble VIII metal. In one embodiment with multiple Group VIII precursors being employed, nickel and cobalt make up at least 50 wt. % of the total of Group VIII non-noble metal components. In another embodiment with multiple Group VIB precursors being employed, molybdenum and tungsten make up at least 50 wt. % of the total of Group VIB metal components.

In one embodiment, the reaction of Group VIB metal and Promoter Metal components is carried out with water-soluble nickel and molybdenum, wherein nickel is used at a ratio of 0.1-1 atom per Mo atom. In a second embodiment, at a ratio of 0.5 nickel atom per each Mo atom.

The metal precursors can be added to the reaction mixture in solution, suspension or as such. If soluble salts are added as such, they will dissolve in the reaction mixture and subsequently be precipitated. In one embodiment, the solution is heated optionally under vacuum to effect precipitation and evaporation of the water.

In one embodiment, in addition to the metal precursors, at least a binder material can be optionally added to the precipitation step. Binder material can be any of the optional binders described above and/or a precursor thereof. If a precursor binder material is added in the form of the solution, process condition can be adjusted so that precipitation of the binder may occur. Additionally in another embodiment, optional materials including but not limited to N-containing/P-containing organic additives, phosphorus-containing compounds, boron-containing compounds, silicon-containing compounds, fluorine-containing compounds, additional transition metal compounds, rare earth metal compounds, or mixtures thereof can be added during precipitation step in a similar way to that described for the above materials.

In one embodiment, the precipitate is subject to activation radiation to further improve the catalyst characteristics. In another embodiment, the precipitate is subject to high intensity ultrasound treatment or electromagnetic energy to reduce the particle size and thus the catalyst characteristics.

In one embodiment prior to the sulfidation step, the precipitate is optionally isolated from the liquid using methods known in the art such as filtration, centrifugation, decantation, or combinations thereof. In another embodiment prior to the sulfidation step, the precipitate is optionally treated with a sulfur additive or a commercially available catalyst presulfiding agent. In yet another embodiment prior to the sulfidation step, the precipitate is optionally treated with at least an N-containing/P-containing organic additive.

Sulfiding Step: The precipitate formed from the reaction of the metal precursors is converted into a sulfided catalyst precursor upon contact with the sulfiding agent. In one embodiment, the sulfidation is carried out at a temperature ranging from 70° C. to 500° C., from 10 minutes to 5 days, and under a $H_2$-containing gas pressure. If the sulfidation temperature is below the boiling point of the sulfiding agent, such as 60-70° C. in the case of ammonium sulfide solution, the process is generally carried out at atmospheric pressure. Above the boiling temperature of the sulfiding agent/optional components, the reaction is generally carried out at an increased pressure, such as in an autoclave.

In one embodiment, optional components such as sulfiding additives and other additives known in the art, e.g., phosphorous-containing promoters can also be added separately or in a mixture with the precipitate and the sulfiding agent. In one embodiment, sulfur additives are added to the mixture of the precipitate and sulfiding agent to increase the incorporation of sulfur in the catalyst.

In one embodiment, the sulfidation is carried out at a temperature ranging from room temperature to 400° C. and for ½ hr. to 24 hours. In another embodiment, the sulfidation is at 150° C. to 300° C. In yet another embodiment, the sulfidation is between 300-400° C. under pressure. In one embodiment, the sulfidation is at between 0 to 3000 psig. In a second embodiment, between 100 to 1000 psig.

In one embodiment, the sulfidation is with an aqueous ammonium sulfide solution at a temperature between 0 and 50° C., and in the presence of at least a sulfur additive selected from the group of thiodazoles, thio acids, thio amides, thiocyanates, thio esters, thio phenols, thiosemicarbazides, thioureas, mercapto alcohols, and mixtures thereof.

In one embodiment with the sulfiding step being carried out in aqueous solution, the resultant product of the sulfiding step is a slurry in an aqueous solution. Analyses will show that the catalyst precursor product of the sulfiding step is catalytically active, although not in optimum form for use in hydroprocessing operations.

In one embodiment, the process can be extended to include blending metal sulfide powders, e.g., molybdenum sulfide powders, into the catalyst precursor to further enhance the activity of the catalyst.

In one embodiment after sulfiding, the catalyst precursor is optionally isolated from the liquid using methods known in the art such as filtration, centrifugation, decantation, or combinations thereof, under an inert atmosphere comprising any of nitrogen, refinery gas, a gas having little or no oxygen, and mixtures thereof. In the next step, the catalyst precursor powder is impregnated again with the sulfiding agent, e.g., ammonium sulfide $(NH_4)_2S$ solution, and/or optional sulfur additives.

In one embodiment after sulfiding, the catalyst precursor is subject to an optional ammonia removal step. Ammonia removal has a favorable effect upon catalyst activity because ammonia is a depressant to the activity of a hydrogenation catalyst. Ammonia removal is beneficial to catalyst activity because any ammonia present can be adsorbed at metal sites and may constitute a catalyst poison. In one embodiment, the sulfided water based slurry from the sulfiding step is subject to a simple aqueous phase ammonia flashing step by cooling and depressurizing the slurry stream. Ammonia can be flashed off together with any generated hydrogen sulfide and hydrogen present in the system.

The hydrogen containing gas in the above steps of the process can be substantially pure hydrogen, or can be mixtures of hydrogen with other gases such as nitrogen, helium, methane, ethane, carbon monoxide or hydrogen sulfide.

Forming Oil-Based Bulk Catalyst Composition: In this step, the catalyst precursor is mixed with a hydrocarbon compound and is transformed into an oil based catalyst of the formula $(M^r)_a(X^u)_b(S^v)_d(C^w)_e(H^x)_f(O^y)_g(N^z)_h$. In one embodiment, the mixing is continuous in a high shear mode, e.g., from 100 to 1600 RPM, and from about 10 minutes to 24 hours, forming a homogeneous slurry. In another embodiment, the reaction time in this step ranges from 30 minutes to 3 hours. In a third embodiment, the reaction time ranges from 1 to 2 hrs.

In one embodiment, the temperature of the transformation step is maintained at a temperature of 50-400° C. In a second embodiment, the temperature is maintained at a temperature of 100-300° C. In one embodiment, the pressure of the transformation step is maintained in the range of 0-1000 psig. In a second embodiment, it is between 200-500 psig. In a third embodiment, from 300-450 psig.

In one embodiment, the mixing is under an inert atmosphere comprising any of nitrogen, refinery gas, a gas having little or no oxygen, and mixtures thereof. In another embodiment, the mixing is under a $H_2$-containing gas pressure. In a third embodiment, hydrogen gas is added at a relatively low rate before and after the reactor in which the hydrocarbon/catalyst precursor mixing takes place. In one embodiment, the $H_2$ flow to the transformation step is kept at 100 to 2000 SCFB ("Standard Cubic Feet per Barrel" of hydrocarbon compound feed to the reactor). In a second embodiment, the $H_2$ flow ranges from 300 to 1000 SCFB.

Ammonia removal from the oil based catalyst can be carried out after the transformation step in one embodiment. The catalyst stream in one embodiment is heated prior to depressurization and ammonia vaporization.

The process steps described herein are in no way limited to the use of any particular apparatus. Any of the reactors for use in the process can be batch, semi-batch, or continuously stirred tank reactors (CSTRs), and can be a vessel equipped heating means having a mechanical stirrer, or a static mixer, or by means of a recirculating pump. The process steps can be operated in any of continuous, batch mode, or combinations there of for some of the steps, using a single-stage reactor or multiple-stage reactors. The components (feed streams) can be introduced simultaneously, or sequentially in any order to the reactor. The term "feed stream" refers to both continuous and batch processed.

In one embodiment, the process is carried out as a batch process with a single reactor being used for the steps, e.g., forming a precipitate, sulfiding, and forming an oil-soluble catalyst in the same equipment, with the steps being carried out in sequence after the completion of the previous step. In another embodiment, the process is a batch process with multiple reactors in series and with each step being carried out in a separate CSTR. In a third embodiment, the process is continuous with the precipitate or catalyst precursor effluents from one step being moved to the next step in the process.

FIG. 1 illustrates the steps involved in one embodiment of the process. In a reactor (mixing tank) 10, at least a group VIB metal precursor such as ammonium heptamolybdate in aqueous solution (feed stream 1) is mixed with at least a Promoter Metal precursor such as nickel sulfate in aqueous solution (feed stream 2), forming a precipitate in aqueous solution (an intermediate mixture). In one embodiment, the reaction time in the mixing tank 10 ranges from about 1 hour to 10 hours. The temperature in one embodiment is maintained at 30° C. to 100° C. at a pressure ranging from 100 to 3000 psig. In one embodiment, the weight ratio of nickel (or cobalt) to molybdenum in the group VIII/group VIB precursor feed streams ranges from about 1:100 to about 1:2. In a second embodiment, the nickel/molybdenum weight ratio ranges from about 1:25 to 1:10.

In one embodiment (not shown), instead of feeding ammonium heptamolybdate in aqueous solution to the reactor 10, metal oxide dissolved in aqueous ammonia solution is used as a feed to the process. In this embodiment, there is an additional mixing zone (not shown) wherein a group VIB metal oxide is dissolved in water containing ammonia at a temperature ranging from 30° C. to 100° C., and at a pressure from atmospheric pressure to about 100 psig. The dissolved metal oxide (e.g., $MoO_3$) in aqueous ammonia is converted to a group VIB metal precursor feed according to the following reaction:

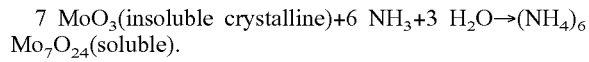

7 $MoO_3$(insoluble crystalline)+6 $NH_3$+3 $H_2O \rightarrow (NH_4)_6 Mo_7O_{24}$(soluble).

The precipitate catalyst precursor precipitate from reactor 10 is moved in line 3 to the next reactor/mixing tank 20, wherein the catalyst precursor is sulfided with a sulfiding agent, e.g., ammonium sulfide $(NH_4)_2S$ for a period of time 5 minutes to 2 hours. In one embodiment, the sulfidation is carried out at a temperature ranging from room temperature to 70° C., and at 0 psig. Optional components (not shown), e.g., N-containing and/or P-containing organic additive, sulfur additives, etc., can be added to reactor 20 to increase the incorporation of sulfur in the catalyst precursor formed in this step.

The water is kept in liquid phase in reactor 20. In one embodiment (not shown), water is changed to vapor phase after reactor 20 in order to flash off the water.

In the next transformation step, the sulfided catalyst precursor from reactor 20 is moved in line 5 to reactor 30, wherein the catalyst precursor slurry is mixed with hydrocarbon oil feed 6, forming an embodiment of the bulk catalyst. Hydrogen is continuously added to the mixture reaction zone, ranging from 300 SCFB ("Standard Cubic Feet per Barrel," meaning per barrel of hydrocarbon feed) to about 2000 SCFB. The pressure of the reaction zone generally ranges from about 100 psig to about 3000 psig. Temperature of the reactor generally ranges from 150 to 300° C. Reactor 30 is a CSTR with high shear mixing of greater 500 RPM ("Revolutions Per Minute") to maintain homogenous slurry in the reactor. The hydrocarbon feed 6 in one embodiment has a kinetic viscosity of 4-10 cSt @ 100° C. The resultant slurry mixture is one embodiment of the active catalyst composition in admixture with the hydrocarbon oil and having the formula $(M^t)_a(X^u)_b(S^v)_d(C^w)_e(H^x)_f(O^y)_g(N^z)_h$.

In one embodiment, the active catalyst composition is moved in line 7 to a storage tank (not shown), wherein the catalyst slurry is continuously mixed in storage tank to maintain a homogenous slurry in a hydrogen atmosphere with little or no oxygen. In this way, the catalyst activity and stability are maintained.

The catalyst composition is useful for upgrading carbonaceous feedstocks which include atmospheric gas oils, vacuum gas oils (VGO), deasphalted oils, olefins, oils derived from tar sands or bitumen, oils derived from coal, heavy crude oils, synthetic oils from Fischer-Tropsch processes, and oils derived from recycled oil wastes and polymers. The catalyst composition is useful for but not limited to hydrogenation upgrading processes such as thermal hydrocracking, hydrotreating, hydrodesulfurization, hydrodenitrification, and hydrodemetalization.

In one embodiment, the bulk catalyst composition is used in a heavy oil upgrading process. As shown in FIG. 1, the catalyst is moved in line 7 to a hydrocracking reactor or ebullated bed catalytic reactor 40, wherein the active catalyst slurry is in contact with a heavy oil 8 (with optional additives such as modifiers, stabilizers, etc.) and a hydrogen-containing gas (not shown) for sufficient time and at appropriate temperature under hydrocracking conditions. The concentration of the active slurry catalyst in the heavy oil feed 8 in one embodiment ranges from about 100 to 20,000 ppm, expressed as weight of metal (molybdenum) to weight of heavy oil feedstock. In one embodiment for a higher conversion for sulfur, nitrogen and metal removal, as well as the higher cracking conversion, a higher catalyst to oil ratio is used. In one embodiment with the use of the catalyst composition, over 95% demetalation conversion and 1000° F. cracking conversion of the heavy oil can be achieved at appropriate process conditions, with a coke yield of less than 1%.

Stream 9 contains combined gas and liquid products (light oil and unconverted heavy oil) as well as catalyst. The resultant light oil is separated from the solid bulk catalyst and unconverted heavy oil in a high pressure separator (not shown). The light oil is sent to a fixed bed reactor typically used for hydrotreating of oil (not shown) to further remove sulfur and nitrogen, and to improve product qualities.

Characterization of the Catalyst: Characterization of the catalyst prepared by the process of the invention can be performed using techniques known in the art, including elemental analysis, Surface Area analysis (BET), Particle Size analysis (PSA), Powder X-ray Diffraction (PXRD), Scanning Electron Microscopy (SEM), Energy Dispersive X-ray Analysis (EDS), and other methods. In one method, electron microscopy is used to complement the x-ray diffraction study. In another method, the surface area of the catalyst is determined using the BET method. In yet another method, scanning tunneling microscopy (STM) and density functional theory (DFT) can be used to characterize the catalyst of the invention. Elemental analysis of the catalyst will show presence of Molybdenum, Nickel, Sulfur, as well as Oxygen, Carbon, Hydrogen, and Nitrogen.

Characteristics of the Catalyst: In one embodiment, the catalyst has a pore volume of 0.05-5 ml/g as determined by nitrogen adsorption. In a second embodiment, the pore volume is 0.1-4 ml/g. In a third embodiment, from 0.1-3 ml/g. In a fourth embodiment, from 0.1-2 ml/g.

In one embodiment, the catalyst has a surface area of at least 5 m$^2$/g. In a second embodiment, a surface area of at least 10 m$^2$/g. In a third embodiment, a surface area of at least 50 m$^2$/g. In a fourth embodiment, the surface area is greater than 100 m$^2$/g as determined via the B.E.T. method. In a fifth embodiment, the catalyst has a surface area of greater than 200 m$^2$/g.

In one embodiment, the catalyst by the process of the invention has an effective suspended median particle size of 0.0005 to 1000 microns. In a second embodiment, the catalyst has a median particle size of 0.001 to 500 microns. In a third embodiment, a particle size of 0.005 to 100 microns. In a fourth embodiment, a particle size of 0.05 to 50 microns. In a fifth embodiment, the catalyst in the form of a dispersed suspension is characterized by a median particle size of 30 nm to 6000 nm. In a six embodiment, the catalyst has an average particle size in the range of 0.3 to 20 µm.

In one embodiment, the catalyst of the formula prepared by the process of the invention is characterized via X-ray powder diffraction (XRD or PXRD) as a poorly crystalline compound having broad diffraction peaks of low intensity. As used herein, a broad peak means a peak having a width at ½ height of more than 1 degree (in 2-θ scale).

In one embodiment, the catalyst is characterized as having at least one broad diffusion peak of >1° (in 2θ scale) at ½ height, at any of Bragg angles (2θ) 8 to 18°, 32 to 40° and 55° to 65° (from 0 to 70° 2θ scale). In another embodiment, the XRD pattern of the catalyst shows at least one broad peak having width at ½ height of >2 degrees (in 2θ scale), with the broad peak being at any of Bragg angles 8-18°, 32-40° and 55-65° in the 2θ scale. In yet another embodiment, XRD pattern of the catalyst shows that at least one broad peak of >=5 degrees wide at ½ height, with the broad peak being at any one of Bragg angles 8-18°, 32-40° and 55-65° in the 2θ scale.

Figure 2:
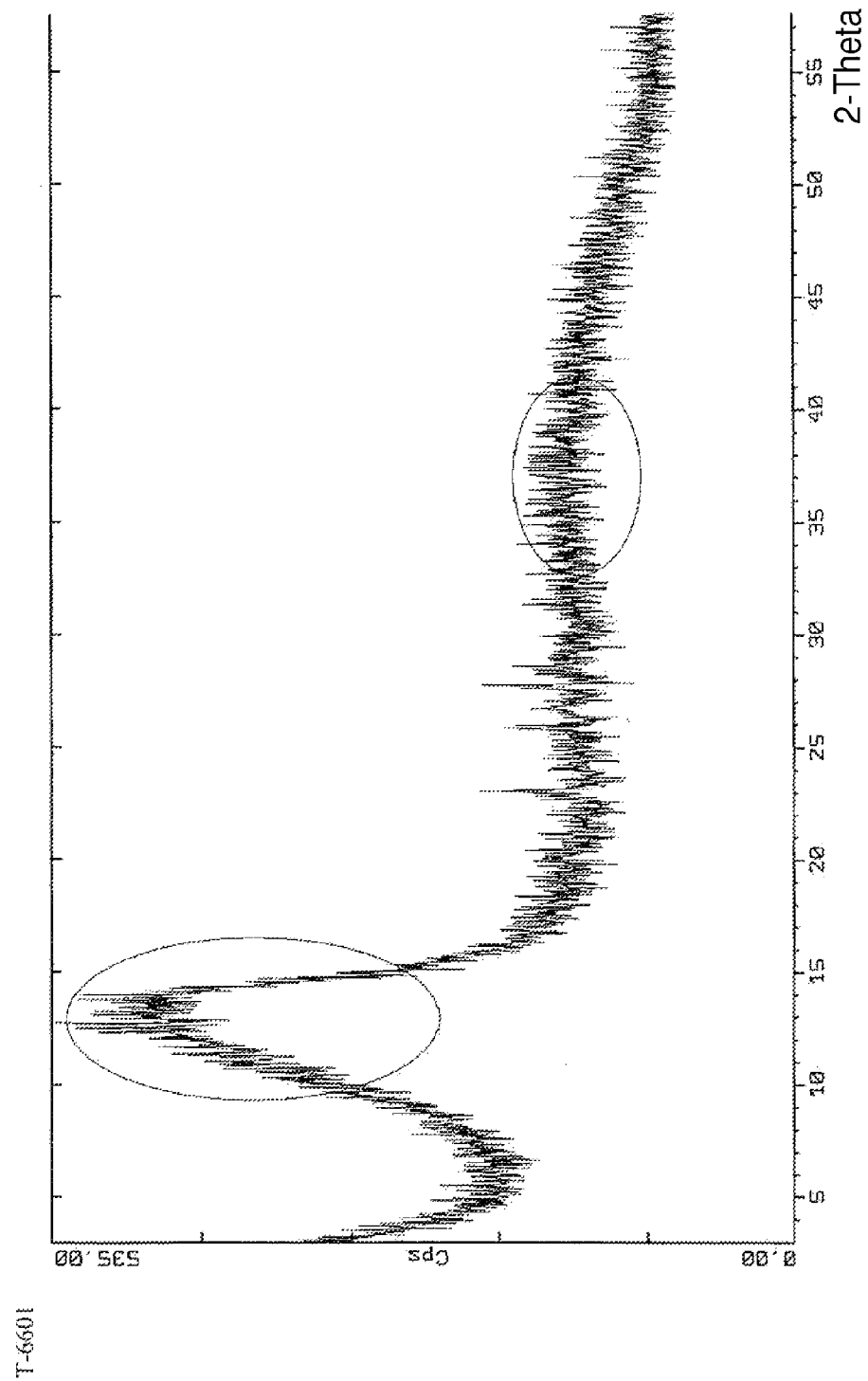
FIG. 2 shows the powder X-ray diffraction pattern of an intermediate catalyst precursor sample in one embodiment of the invention, showing a complex mixture of poorly crystalline compounds with broad spectra, multiple diffraction peaks of low intensity in the PXRD spectrum indicating small crystallite size.
Figure 3:
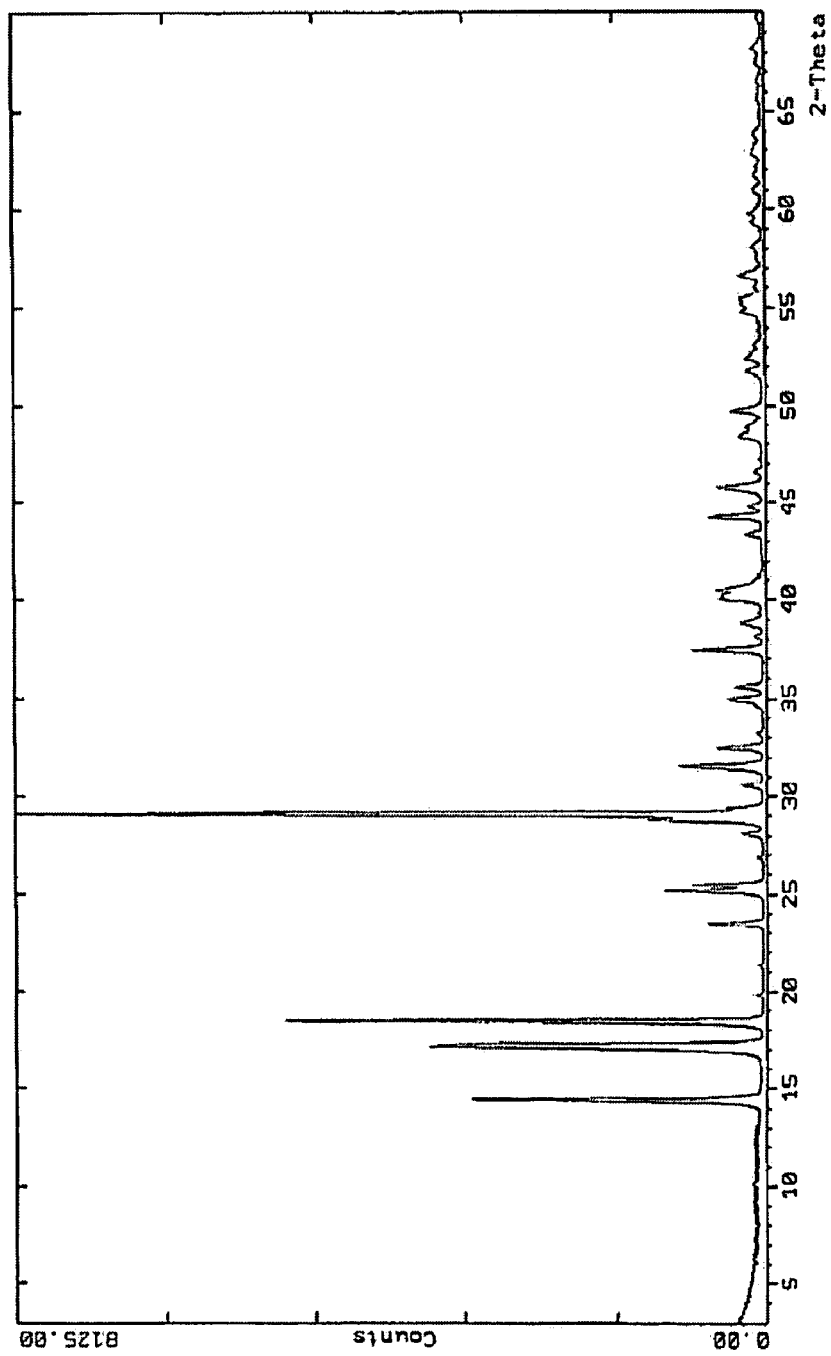
FIG. 3 is a PXRD spectrum of a comparative stock crystalline ammonium tetrathiomolybdate.

FIG. 2 shows the powder X-ray diffraction pattern of the intermediate catalyst precursor sample from one embodiment of the invention (solids filtered from the water-based pre-catalyst slurry of Example 1), with a broad peak appearing between 7-17 degrees and also between 33-43 degrees (in 2θ scale) and also as indicated by circles on the figure. For comparison, a PXRD spectrum of stock crystalline ammonium tetrathiomolybdate is shown in FIG. 3 with narrow and well-defined peaks being observed at 14-15 and 28 degrees (in 2θ scale).

Figure 4:
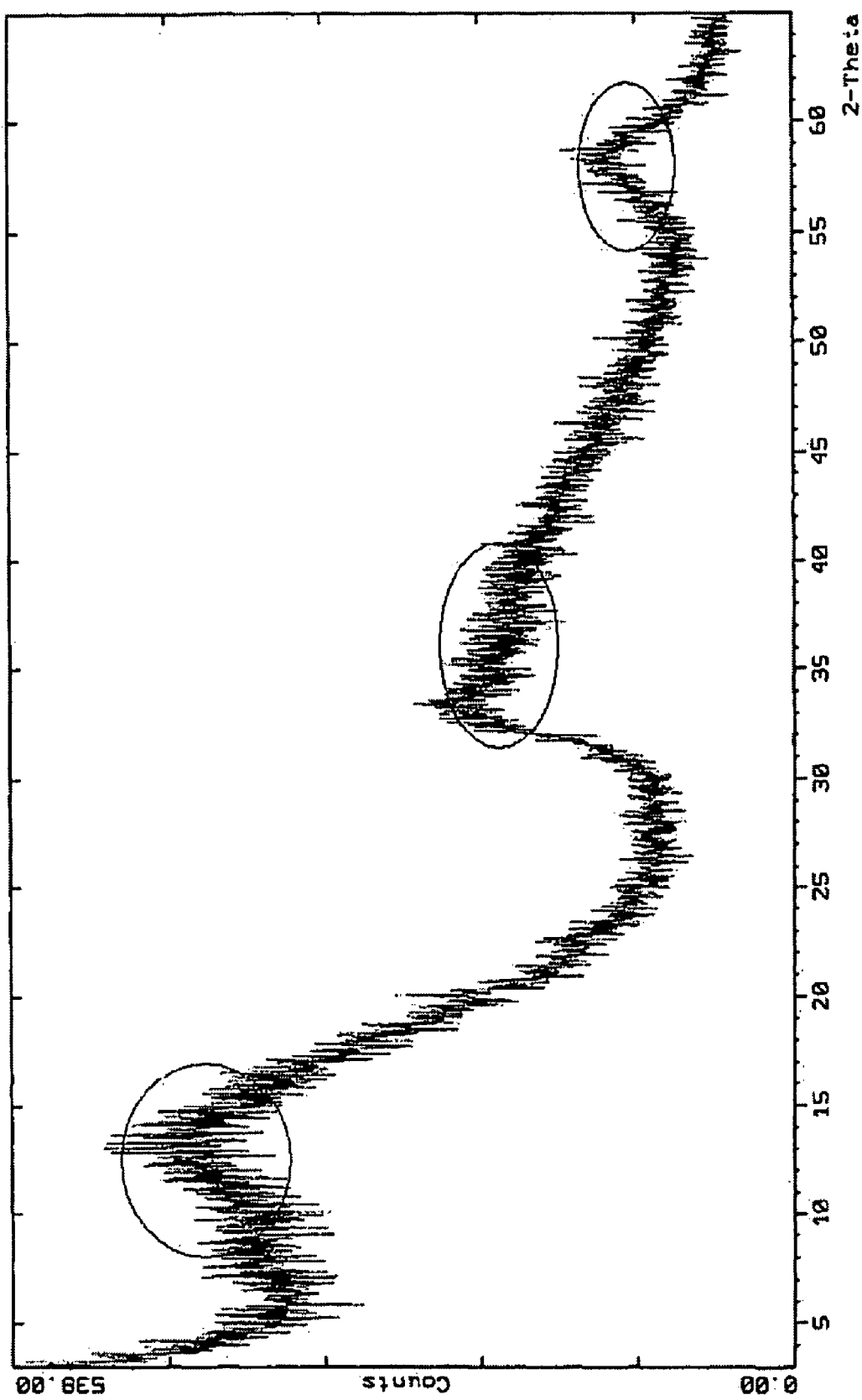
FIG. 4 shows the powder X-ray diffraction pattern of a catalyst sample in one embodiment of the invention, showing poor crystallinity with diffuse Bragg peaks (width of peaks at ½ height is >>1° in 2-theta scale).
Figure 5:
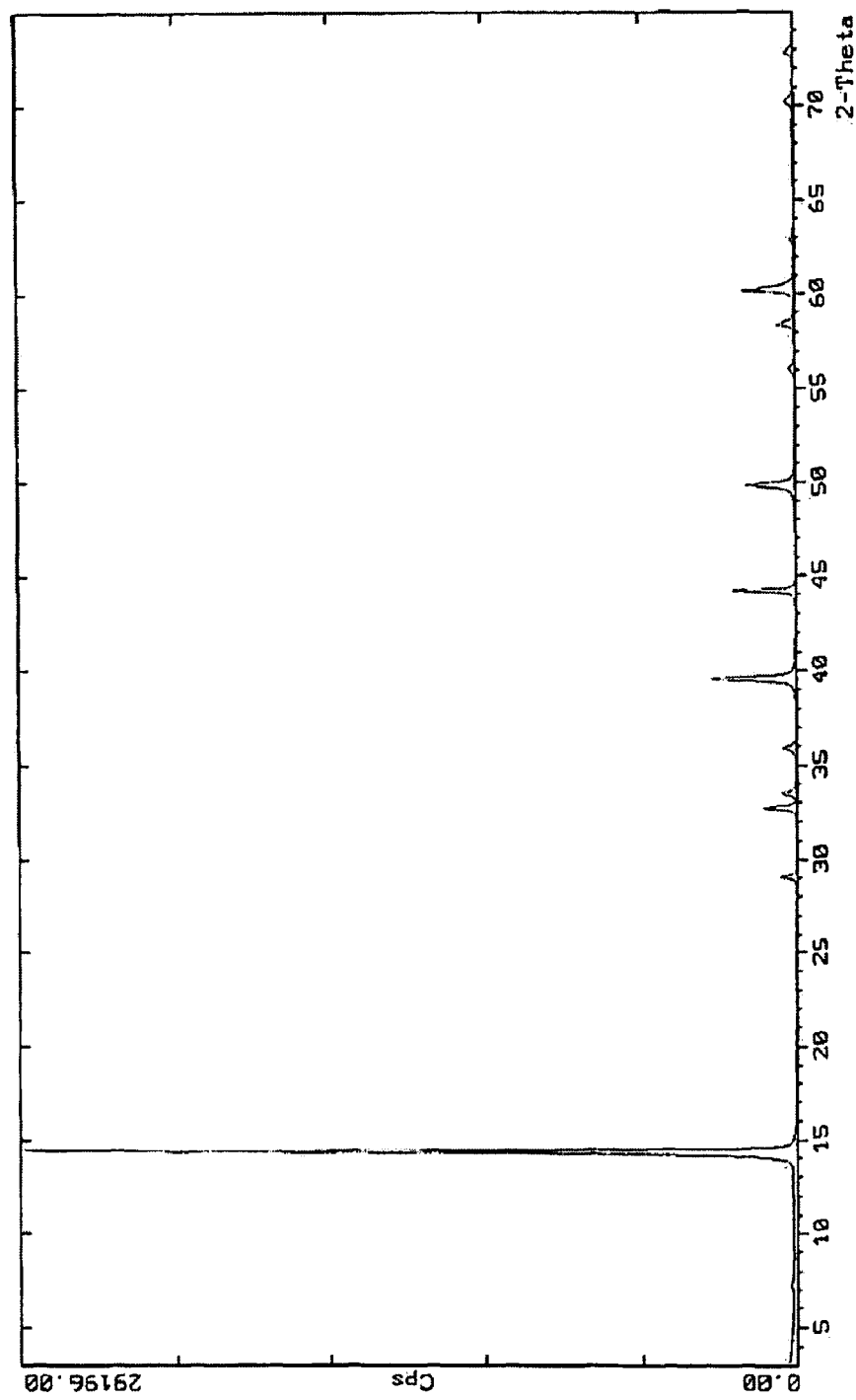
FIG. 5 show a PXRD spectrum of a comparative crystalline $MoS_2$ with well-defined diffraction peaks of high intensity.

FIG. 4 shows the powder X-ray diffraction pattern of a catalyst sample in one embodiment of the invention (prepared along the line of Example 10). X-ray diffraction analyses show that the catalyst exhibits poor crystallinity with diffuse/broad Bragg peaks (width of peaks at ½ height is >1° in 2-theta scale) at 8-15°, 32-40° and 55-65°. For comparison, FIG. 5 shows a PXRD spectrum of crystalline MoS$_2$ with well-defined diffraction peaks of high intensity. Catalytic activity of this material is much lower than that of a catalyst in an embodiment of the invention.

Figure 6:
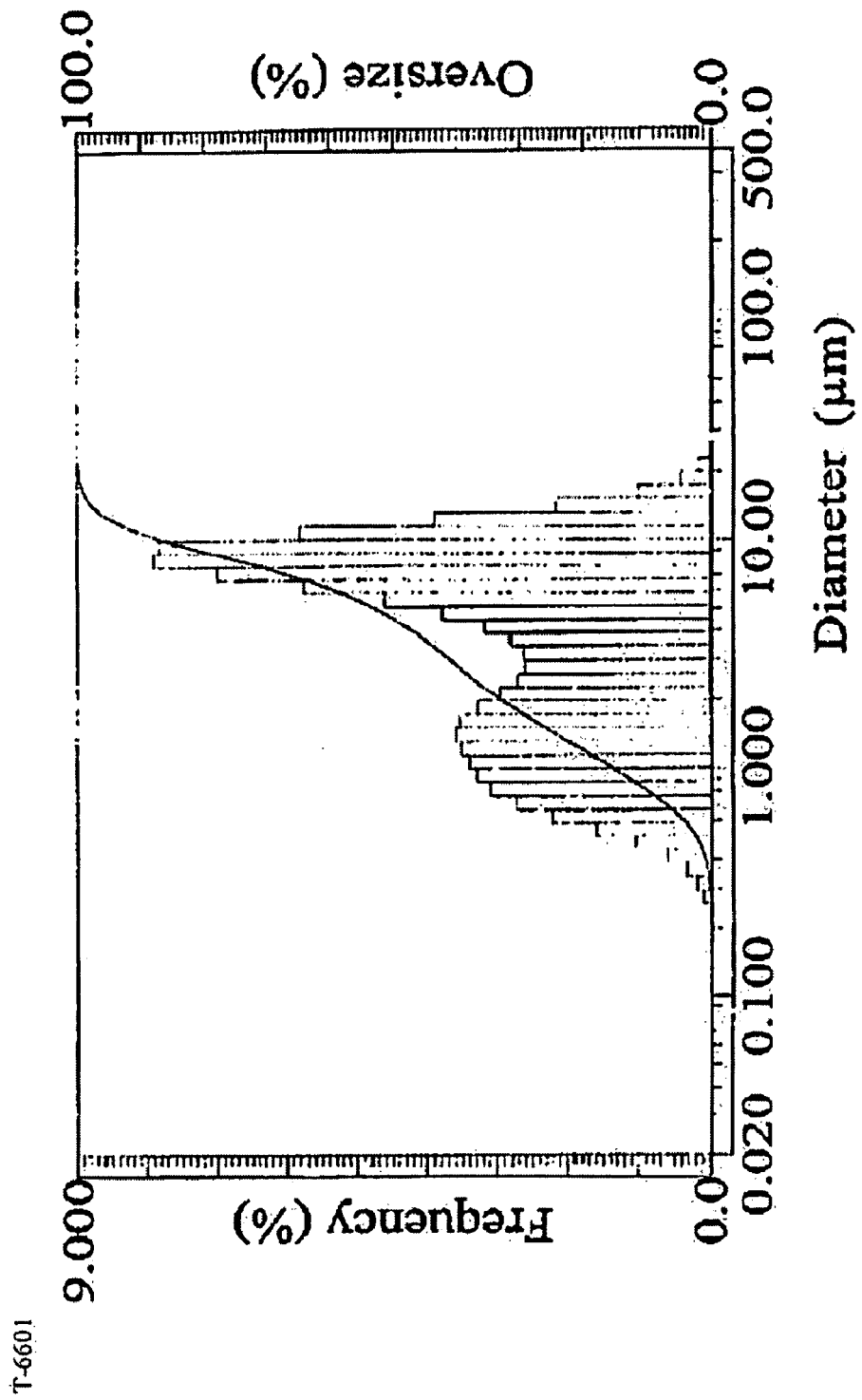
FIG. 6 shows volume-based particle size analysis of an embodiment of a catalyst compound of the invention.

FIG. 6 shows a volume-based PSA spectrum of extracted catalyst solids of one embodiment of the invention. Most of the particles fall into the 0.3 to 20 µm average particle size range, with peak distribution frequencies at 1 µm and 10 µm, suggesting a bi-modal type distribution.

Use of The Catalyst: The catalyst composition can be used in virtually all hydroprocessing processes to treat a plurality of feeds under wide-ranging reaction conditions such as temperatures of from 200 to 450° C., hydrogen pressures of from 5 to 300 bar, liquid hourly space velocities of from 0.05 to 10 h$^{-1}$ and hydrogen treat gas rates of from 35.6 to 1780 m$^3$/m$^3$ (200 to 10000 SCF/B). The hydroprocessing can be practiced in one or more reaction zones and can be practiced in either countercurrent flow or cocurrent flow mode. By countercurrent flow mode is meant a process wherein the feedstream flows countercurrent to the flow of hydrogen-containing treat gas. The hydroprocessing also includes slurry and ebullated bed hydrotreating processes for the removal of sulfur and nitrogen compounds and the hydrogenation of aromatic molecules present in light fossil fuels such as petroleum mid-distillates, e.g., hydrotreating a heavy oil employing a circulating slurry catalyst.

The feeds for use in hydroprocessing processes using the catalyst may include petroleum and chemical feedstocks such as olefins, reduced crudes, hydrocrackates, raffinates, hydrotreated oils, atmospheric and vacuum gas oils, coker gas oils, atmospheric and vacuum resids, deasphalted oils, dewaxed oils, slack waxes, Fischer-Tropsch waxes and mixtures thereof. Specific examples range from the relatively light distillate fractions up to high boiling stocks such as whole crude petroleum, reduced crudes, vacuum tower residua, propane deasphalted residua, brightstock, cycle oils, FCC tower bottoms, gas oils including coker gas oils and vacuum gas oils, deasphalted residua and other heavy oils. In one embodiment, the feedstock is a $C_{10+}$ feedstock. In another the feedstock is selected from distillate stocks, such as gas oils, kerosenes, jet fuels, lubricating oil stocks boiling above 230° C., heating oils, hydrotreated oil stock, furfural-extracted lubricating oil stock and other distillate fractions whose pour point and viscosity properties need to be maintained within certain specification limits.

In one embodiment, the feedstocks contain a substantial amount of nitrogen, e.g. at least 10 wppm nitrogen, in the form of organic nitrogen compounds. The feeds can also have a significant sulfur content, ranging from about 0.1 wt. % to 3 wt. %, or higher. In yet another embodiment, the feedstock is a feed derived from crude oils, shale oils and tar sands as well as synthetic feeds such as those derived from the Fischer-Tropsch process, having initial boiling points of greater than 315° C. or higher. Specific examples include reduced crudes, hydrocrackates, raffinates, hydrotreated oils, atmospheric gas oils, vacuum gas oils, coker gas oils, atmospheric and vacuum resids, deasphalted oils, slack waxes and Fischer-Tropsch wax, and mixtures thereof. In one embodiment, the feedstock is a mixture of gas oil from a coker and vacuum distillation from conventional crudes, derived from distillation towers (atmospheric and vacuum), hydrocrackers, hydrotreaters and solvent extraction units, and may have wax contents of up to 50% or more. In yet another embodiment, the feed stock is selected from mid-distillates from fossil fuels such as light catalytic cycle cracking oils (LCCO); distillates derived from petroleum, coal, bitumen, tar sands, or shale oil; heavy catalytic cracking cycle oils (HCCO), coker gas oils, oils derived from recycled oil wastes and polymers, vacuum gas oils (VGO) and heavier resids, which contain several percent 3+ ring aromatics, particularly large asphaltenic molecules.

The hydrotreating processes using the catalyst may be suitable for making lubricating oil basestocks meeting Group II or Group III base oil requirements. In one embodiment, the catalyst is for use in a hydroprocessing process producing white oils. White mineral oils, called white oils, are colorless, transparent, oily liquids obtained by the refining of crude petroleum feedstocks.

The catalyst can be applied in any reactor type. In one embodiment, the catalyst is applied to a fixed bed reactor. In another embodiment, two or more reactors containing the catalyst may be used in series.

In one embodiment, the catalyst is added to the feedstock (catalyst to oil ratio) at a rate of 0.01 to 3 wt. %. In a second embodiment, at a rate of 0.25 to 2 wt. %. In a third embodiment, at a rate of 100 to 2000 ppm active metals, i.e., the group VIB metals "M" in the formula $(M^t)_a(X^u)_b(S^v)_d(C^w)_e(H^x)_f(O^y)_g(N^z)_h$. In a fourth embodiment, the catalyst is added to the feedstock at a sufficient rate for the total amount of Mo in the reaction zone reaches 0.005 to 0.05 wt. % (based on the total weight of the feedstock).

In one embodiment of a hydrogenation process employing the catalyst of the formula $(M^t)_a(X^u)_b(S^v)_d(C^w)_e(H^x)_f(O^y)_g(N^z)_h$, the heavy hydrocarbon is hydrogenated to a value of up to 90% by mass.

EXAMPLES

The following illustrative examples are intended to be non-limiting. Unless specified otherwise, the catalytic activity of the catalysts prepared in the examples are tested for Hydrodenitrogenation (HDN), Hydrodesulfurization (HDS), as well as API gravity change and Microcrystalline Carbon Residue (MCRT). The results are presented in Table 2.

Example 1

(base example): 33.12 g of ammonium heptamolybdate tetrahydrate $((NH_4)_6Mo_7O_{24})$ was dissolved in 100 g of water in a glass vessel fitted with an overhead mechanical stirrer, and 14.1 g of concentrated ammonia solution (28 wt. % $NH_4OH$ in $H_2O$) was added. A solution of 8.1 g of nickel sulfate hexahydrate $(NiSO_4.6H_2O)$ in 32 g of water was added to the first solution, all at ambient temperature, producing an emerald-green suspension. This suspension was heated to 70° C. under atmospheric pressure, and 101 g of ammonium sulfide $((NH_4)_2S)$ solution in water (40-44 wt. %) was added slowly, over the course of 45 minutes. After that, the mixture was heated with stirring for an additional 60 minutes. The volume of the reaction mixture was reduced in half on a rotary evaporator. The resulting water-based catalyst precursor was transformed to a final oil-based catalyst with medium cycle oil (MCO) and hydrogen in a pressure test autoclave in situ.

Example 2

(lower ammonia concentration): The procedure is similar to Example 1, using 33.12 g of ammonium heptamolybdate tetrahydrate to dissolve in 100 g of water in a glass vessel fitted with an overhead mechanical stirrer, and in this case 5 g of concentrated ammonia solution was added. A solution of 8.1 g of nickel sulfate hexahydrate in 32 g water was added to the first solution, all at ambient temperature, producing a light-green suspension. This suspension was heated to 70° C. under atmospheric pressure, and 101 g of ammonium sulfide solution was added slowly, over the course of 45 minutes. After that, the mixture was heated with stirring for an additional 60 minutes. The rest of the procedures and tests were similar to Example 1.

Example 3

(higher ammonia concentration: 8.1 g of nickel sulfate hexahydrate was dissolved at ambient temperature in a mixture of 100 g of water and 15.3 g of concentrated ammonia solution in a glass vessel fitted with an overhead mechanical stirrer. Then, 33.12 g of ammonium heptamolybdate tetrahydrate was added to this mixture, forming a green suspension. Additional 11.4 g of ammonia solution was added, to yield a clear deep-blue solution. This solution was heated to 70° C. under atmospheric pressure, and 101 g of ammonium sulfide solution in was added slowly, over the course of 45 minutes. After that, the mixture was heated with stirring for an additional 60 minutes. The rest of the procedures and tests were similar to Example 1.

Example 4

(very low ammonia-concentration, solid AHM added): 8.1 g of nickel sulfate hexahydrate was dissolved at ambient temperature in a mixture of 100 mL of water and 0.2 g of concentrated ammonia solution in a glass vessel fitted with an overhead mechanical stirrer. Then, 33.12 g of ammonium heptamolybdate tetrahydrate was added to this mixture, forming a heavy light-green suspension. This solution was heated to 70° C. under atmospheric pressure, and 101 g of ammonium sulfide solution was added slowly, over the course of 45 minutes. After that, the mixture was heated with stirring for an additional 60 minutes. The rest of the procedures and tests were similar to Example 1.

Example 5

(slow addition of sulfiding reagent): The procedure is similar to Example 2, using 33.12 g of ammonium heptamolybdate tetrahydrate to dissolve in 100 g of water with 5 g of concentrated ammonia solution, in a glass vessel fitted with an overhead mechanical stirrer. A solution of 8.1 g of nickel sulfate hexahydrate in 32 g water was added to the first solution, all at ambient temperature, producing a light-green suspension. This suspension was heated to 70° C. under atmospheric pressure, and 101 g of ammonium sulfide solution was added slowly, over the course of 120 minutes. After that, the reaction was stopped, and the rest of the procedures and tests were similar to Example 1.

Example 6

(rapid addition of sulfiding reagent, with continued heating): The procedure is similar to Example 5, except that the addition of 101 g of ammonium sulfide solution was done over 3 minutes. After that, the reaction was heated with stirring for an additional 120 minutes, and the rest of the procedures and tests were similar to Example 1.

Example 7

(rapid addition of sulfiding reagent): The procedure is similar to Example 1, except that the addition of 101 g of ammonium sulfide solution was done over 10 minutes, and the reaction was stopped immediately after that. The rest of the procedures and tests were similar to Example 1.

Example 8

(higher amount of nickel relative to molybdenum—Mo:Ni=5:1): The procedure is similar to Example 2, using 33.12 g of ammonium heptamolybdate tetrahydrate to dissolve in 100 g of water mixed with 5 g of concentrated ammonia solution, in a glass vessel fitted with an overhead mechanical stirrer. A solution of 16.2 g of nickel sulfate hexahydrate in 32 g water was added to the first solution, all at ambient temperature, producing a green suspension. This suspension was heated to 70° C. under atmospheric pressure, and 100 g of ammonium sulfide solution (44 wt. %) was added slowly, over the course of 45 minutes. After that, the mixture was heated with stirring for an additional 60 minutes. The rest of the procedures and tests were similar to Example 1.

Example 9

(higher amount of nickel relative to molybdenum—Mo:Ni =3:1): The procedure was similar to Example 2, however 26.9 g of nickel sulfate hexahydrate solution in 39 g water, was used, producing a green-yellow suspension in the first step. Further procedures and tests were similar to Example 1.

Example 10

(large-scale synthesis of oil transformed catalyst): 2663 g of ammonium dimolybdate was combined with 1850 g of hot deionized (DI) water, and 1566 g of ammonium hydroxide solution (28% in water). The mixture was stirred and the reactor heated to ~140° F. After stirring for 20 minutes, a slurry of 673 g of nickel sulfate hexahydrate in 667 g of ammonium hydroxide (28% in water) was added. The mixture was stirred for four hours to dissolve any solids present. At this time the reaction mixture was a dark blue solution. An aqueous ammonium sulfide solution (41.9%) was added via a peristaltic tube pump with an addition speed of ~91 g.min−1. A total of 9061 g of ammonium sulfide solution was added over 100 minutes.

The bulk of the water-based catalyst precursor was subjected to batch transformation, by mixing 3796 g of aqueous based precursor and 3000 g of vacuum gas oil (VGO) in a 3-gallon autoclave and heating to 400° F. under 400 psi of nitrogen. Then hydrogen was added with 32 SCF/h and the reduction was carried out until no $H_2S$ was detected in the exit gas stream. This gave the final catalyst slurry was tested with medium cycle oil (MCO) and hydrogen in a pressure test autoclave for HDN/HDS/API/MCRT activity.

Example 11

(reduced amount of water, hydrazine additive): 8.22 g of nickel sulfate hexahydrate were dissolved in 20 g of DI water, followed by the addition of 8.05 g of 28% ammonium hydroxide solution. A dark blue clear solution formed, pH=9.6 at 25° C. In a separate container 18 g of 28% ammonium hydroxide solution was mixed with 12 g of DI water. 33.13 g of ammonium heptamolybdate tetrahydrate (AHM) was added to the above solution with stirring. The resulting mixture was heated in a water bath at 40° C. for 15 min followed by the addition of nickel sulfate solution. The pH was adjusted to 8.5 with 2 ml of concentrated ammonium hydroxide solution. As the result a clear solution was obtained. The solution was heated to 80° C. under ambient pressure. 94.48 g of ammonium sulfate solution (~50% wt.) was added slowly, over the course of 1 hr. The mixture was kept for additional 30 min at 80° C. followed by addition of 30 ml of hydrazine. The mixture was stirred for 2 hrs and then cooled down to room temperature. The final pH was 9.1. The rest of the procedures and tests were similar to Example 1, except the final product was sonicated for 5 min.

Example 12

(Cobalt/Molybdenum catalyst): 6.03 g of 28% ammonium hydroxide solution was added to 44.01 g of DI water. The solution was heated to 60 C. 33.12 g of ammonium heptamolybdate tetrahydrate was added to the above solution and stirred till clear. The resulting solution was heated to 70 C, pH=6.6 at 60 C, and 92.03 g of concentrated ammonium sulfide (50% wt) solution was added slowly over the course of 45 min followed by the addition of 7.8 g of cobalt acetate tetrahydrate. The mixture was stirred for another 2 hrs at 75 C and then cooled to room temperature. The rest of the procedures and tests were similar to Example 1.

Example 13

(Nickel/Molybdenum/Tungsten catalyst, 6% wt Mo/13% wt W/8% wt Ni): 17.65 g of ammonium heptamolybdate tetrahydrate (($NH_4)_6Mo_7O_{24}$) was dissolved in 800 g of water in a glass vessel fitted with an overhead mechanical stirrer. 24.66 g of ammonium metatungstate hydrate was added to the above solution, pH=5.3 at 22° C. The pH was adjusted to 9.7 with 30 ml of 28% wt. ammonium hydroxide and the solution was heated to 90 C. 58.21 g of nickel sulfate hexahydrate ($NiSO_4.6H_2O$) was dissolved in 50 g of DI water, heated to 90° C., and added to the first solution. A resulting suspension was stirred at the temperature for 60 min. and then filtered hot to produce an apple green filter cake. The cake was washed with DI water and 109 g of it were mixed with 103 g of DI water, sonicated for 20 min, and heated to 70° C. under atmospheric pressure followed by addition of 100 g of ammonium sulfide (($NH_4)_2S$) solution in water (50 wt. %) over the course of 60 minutes. After that, the mixture was heated with stirring for an additional 60 minutes. The rest of the procedures and tests were similar to Example 1.

Example 14

Catalyst Screening Studies: In this example, the feed consists of highly aromatic FCC ("fluidized catalyst cracking") cycle oil which has the aromatic complexity of heavy oil but without the difficult to analyze asphalt. The operating conditions are as follows: 725° F. for reaction temperature, an equivalent of 3000 SCFB hydrogen to oil ratio, 1250 psig Hydrogen Partial Pressure, 4 hours residence time, and catalyst to oil ratio equal to 1.8 percent by weight of feed.

These conditions, although consistent with those usually employed in cycle oil hydrogenation units are substantially more demanding because of the very low catalyst to oil ratio used in this study. Table 1 summarizes both the operating conditions used as well as the quality of the screening feed.

TABLE 1

| Catalyst Screening Conditions and Feed Inspections. | |
|---|---|
| Catalyst Screening Conditions: | |
| Catalyst to Oil Ratio, wt/wt, % | 1.8 |
| Temperature Protocol: | |
| Ramp to CAT, Hrs (F/Min.) | 2.5 (5.0) |
| CAT, F | 725 |

TABLE 1-continued

Catalyst Screening Conditions and Feed Inspections.

| | |
|---|---|
| Soak at CAT, Hrs | 4.0 |
| Quench, Time, Minutes for 450 F CAT | 1.0 |
| Initial Pressure, psig | 1050 |
| Final Pressure, psig | Measure |

TABLE 1-continued

Catalyst Screening Conditions and Feed Inspections.

| | |
|---|---|
| Hydrogen Partial Pressure: | |
| Calculated @ CAT, psi | 1250 |
| Hydrogen/Oil Ratio, SCFB | 3000 |
| Feed: 50/50 Blend of LCO/MCO: | PGQ2889 |
| Inspections: | |
| API Gravity | 7.7 |
| Sulfur, PPM | 9580 |
| Nitrogen, PPM | 1670 |
| Refractive Index @ 20 C. | 1.6068 |
| Aromatic Carbon by ndM, % | 86.9 |
| Distillation, D2887 | |
| 10% @ | 534 |
| 50% @ | 666 |
| 90% @ | 847 |
| EP | 1141 |
| Characterization Factor | 10.26 |

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items.

This written description uses examples to disclose the invention, including the best mode, and also to enable any person skilled in the art to make and use the invention. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

TABLE 2

| | Feed no catalyst | Feed + water no catalyst | 1 | 2 | 3 | 4 | 5 | 6 |
|---|---|---|---|---|---|---|---|---|
| API gravity | 7.5 | 10.5 | 13.3 | 13.1 | 13.0 | 12.8 | 13.1 | 13.2 |
| HDN, ppm N | 1730 | 1443 | 531 | 564 | 698 | 735 | 538 | 547 |
| HDS wt. % S | 0.93 | 0.79 | 0.22 | 0.24 | 0.19 | 0.21 | 0.22 | 0.23 |
| MCRT wt % | — | — | 0.98 | 1.00 | 1.16 | 1.13 | 0.96 | 0.96 |

| | 7 | 8 | 9 | 10 | 11 | 12 | 13 |
|---|---|---|---|---|---|---|---|
| API gravity | 12.7 | 13.0 | 13.3 | 14.7 | 14.3 | 13.6 | 12.9 |
| HDN, ppm N | 634 | 404 | 507 | 402 | 305 | 490 | 849 |
| HDS wt. % S | 0.29 | 0.17 | 0.17 | 0.21 | 0.15 | 0.28 | 0.29 |
| MCRT wt % | 1.33 | 0.91 | 0.93 | — | — | — | — |

The invention claimed is:

1. A process for preparing a hydroprocessing catalyst composition, which process comprising the steps of:
    i) combining and reacting at least one Group VIB metal compound ("M") with at least a metal compound ("Promoter Metal" compound X) selected from a non-noble Group VIII metal, a Group VIIIB metal, a Group VIB metal, a Group IVB metal, and a Group IIB metal to obtain an intermediate mixture;
    ii) sulfiding the intermediate mixture with a sulfiding agent in solution forming a catalyst precursor; and
    iii) mixing the catalyst precursor with a hydrocarbon compound to form a hydroprocessing catalyst composition having formula $(M^t)_a(X^u)_b(S^v)_d(C^w)_e(H^x)_f(O^y)_g(N^z)_h$, wherein
    subscripts a and b each are suitably greater than 0 such that $0 \leq b/a \leq 5$, $0 \leq f \leq 7(a+b)$, $0 \leq g \leq 5(a+b)$, $0 \leq h \leq 0.5(a+b)$,
    the molar ratio of the sulfiding agent to the at least one Group VIB metal compound M and the at least a Promoter Metal compound X is sufficient for subscript d to have a value of: $(a+0.5b) \leq d \leq (5a+2b)$,
    t, u, v, w, x, y, z, each representing total charge for each of: M, X, S, C, H, O and N, respectively,
    $ta+ub+vd+we+xf+yg+zh=0$; and
    the catalyst precursor is mixed with a sufficient amount of hydrocarbon for subscript e to have a value of $0 \leq e \leq 11(a+b)$.

2. The process of claim 1, wherein the hydroprocessing catalyst has an X-ray powder diffraction pattern with at least one broad diffraction peak at any of Bragg angles: 8 to 18°, 32 to 40°, and 55 to 65° (from 0 to 70° 2θ scale).

3. The process of claim 2, wherein the at least one broad diffraction peak is greater than 2 degrees wide at ½ height.

4. The process of claim 2, wherein the catalyst has at least one broad diffraction peak at Bragg angle of 8 to 18° (from 0 to 70° 2θ scale).

5. The process of claim 4, wherein the broad diffraction peak at Bragg angle 8 to 18° (from 0 to 70° 2θ scale) is greater than 2 degrees wide at ½ height.

6. The process of claim 5, wherein the broad diffraction peak at Bragg angle 8 to 18° (from 0 to 70° 2θ scale) is greater than 5 degrees wide at ½ height.

7. The process of claim 1, wherein the catalyst has a median particle size of 0.0005 to 1000 microns.

8. The process of claim 6, wherein the catalyst has an average particle size of 0.3 to 20 μm.

9. The process of claim 7, wherein the catalyst has a pore volume of 0.05-5 ml/g as determined by nitrogen adsorption.

10. The process of claim 1, wherein the intermediate mixture is a non-homogenous suspension.

11. The process of claim 1, wherein the catalytic precursor is a slurry.

12. The process of claim 1, wherein the sulfiding agent is ammonium sulfide in aqueous solution.

13. The process of claim 1, wherein the intermediate mixture is a clear homogenous solution.

14. The process of claim 1, wherein the intermediate mixture is a non-homogenous suspension.

15. The process of claim 1, wherein the reaction of the at least one Group VIB metal compound with the at least one Promoter Metal compound is at 0° C. to 300° C. and at a pressure ranging from 0 to 3000 psig.

16. The process of claim 1, wherein the at least one Group VIB metal is molybdenum and the at least one Promoter Metal is nickel.

17. The process of claim 1, wherein the at least one Group VIB metal compound is molybdenum, the at least one Promoter Metal compound is nickel, the weight ratio of nickel to molybdenum is about 1:100 to about 1:2.

18. The process of claim 1, wherein the intermediate mixture is sulfided with a sulfiding agent selected from the group of ammonium sulfide, ammonium polysulfide ($[(NH_4)_2S_x]$), ammonium thiosulfate (($NH_4)_2S_2O_3$), sodium thiosulfate $Na_2S_2O_3$), thiourea $CSN_2H_4$, carbon disulfide, dimethyl disulfide (DMDS), dimethyl sulfide (DMS), tertiarybutyl polysulfide (PSTB) and tertiarynonyl polysulfide (PSTN), and mixtures thereof.

19. The process of claim 1, wherein the intermediate mixture is sulfided with ammonium sulfide $(NH_4)_2S$ for a period of time 5 minutes to 5 hours at a temperature from 20 to 100° C., and at 0-100 psig.

20. The process of claim 1, wherein the catalyst precursor is mixed with the hydrocarbon compound at a temperature of 100 -300° C. and at a pressure of 0 -1000 psig, forming the hydroprocessing catalyst of formula $(M^t)_a(X^u)_b(S^v)_d(C^w)_e(H^x)_f(O^y)_g(N^z)_h$.

21. The process of claim 1, wherein the step of combining and reacting the at least one of a Group VIB metal compound with the at least a Promoter Metal compound to obtain an intermediate mixture comprises:

mixing at least a Group VIB metal oxide and aqueous ammonia to form at least a Group VIB metal compound in aqueous solution;

reacting the at least a Group VIB metal compound in aqueous solution with the at least one Promoter Metal compound to form the intermediate mixture.

* * * * *